United States Patent
Miao et al.

(10) Patent No.: US 10,342,852 B2
(45) Date of Patent: Jul. 9, 2019

(54) METHODS OF REDUCING BLOOD GLUCOSE OR TRIGLYCERIDE LEVELS BY ADMINISTRATION OF METRNL PROTEIN

(71) Applicants: Chaoyu Miao, Shanghai (CN); Zhiyong Li, Shanghai (CN); Pei Wang, Shanghai (CN)

(72) Inventors: Chaoyu Miao, Shanghai (CN); Zhiyong Li, Shanghai (CN); Pei Wang, Shanghai (CN)

(73) Assignees: Chaoyu Miao, Shanghai (CN); Zhiyong Li, Shanghai (CN); Pei Wang, Shanghai (CN)

(*) Notice: Subject to any disclaimer, the term of this patent is extended or adjusted under 35 U.S.C. 154(b) by 110 days.

(21) Appl. No.: 15/729,420

(22) Filed: Oct. 10, 2017

(65) Prior Publication Data

US 2018/0030102 A1 Feb. 1, 2018

Related U.S. Application Data

(60) Division of application No. 15/137,606, filed on Apr. 25, 2016, now abandoned, which is a continuation of application No. PCT/CN2014/000949, filed on Oct. 27, 2014.

(30) Foreign Application Priority Data

Oct. 29, 2013 (CN) .......................... 2013 1 0525181
Oct. 29, 2013 (CN) .......................... 2013 1 0525184

(51) Int. Cl.
| | | |
|---|---|---|
| *A61K 38/19* | (2006.01) | |
| *C07K 14/52* | (2006.01) | |
| *A61K 38/22* | (2006.01) | |
| *A23L 33/17* | (2016.01) | |
| *A61K 39/00* | (2006.01) | |
| *C07K 14/475* | (2006.01) | |

(52) U.S. Cl.
CPC .............. *A61K 38/19* (2013.01); *C07K 14/52* (2013.01); *A23L 33/17* (2016.08); *A23V 2002/00* (2013.01); *A61K 38/22* (2013.01); *A61K 39/00* (2013.01); *C07K 14/475* (2013.01)

(58) Field of Classification Search
None
See application file for complete search history.

(56) References Cited

U.S. PATENT DOCUMENTS

2011/0112035 A1  5/2011  Jorgensen et al.

FOREIGN PATENT DOCUMENTS

| CN | 102164611 A | 8/2011 |
| CN | 103536903 A | 1/2014 |
| CN | 103536904 A | 1/2014 |
| WO | 2014116556 A2 | 7/2014 |

OTHER PUBLICATIONS

Vezyraki et al. Biochem Biophys Res Commun. Jul. 13, 2013.*
Li et al. CNS Neuroscience & Therapeutics 20: 344-354, 2014.*
Dec. 1, 2002—"Increased lipolysis in transgenic animals overexpressing the epithelial fatty acid binding protein in adipose cells"—Herzel, A. V. et al—Journal of Lipid Research.
Jun. 5, 2008—"Effect of Des-acyl Ghrelin on Adiposity and Glucose Metabolism"—Zhang, weizhen et al—Endocrinology.
Jan. 15, 2013—"Construction and phenotype analysis of adipose tissue-specific PID1expression transgenic mice"—Zhu, Jin'gai—China Doctoral Dissertations Full-Text Database.
Jan. 28, 2015—International Search Report and WO—PCT App PCT/CN2014/000949.

* cited by examiner

*Primary Examiner* — Christine J Saoud
(74) *Attorney, Agent, or Firm* — Banner & Witcoff, Ltd.

(57) ABSTRACT

The present invention provides an application of Metrnl protein in preparing a hypolipidemic, hypoglycemic medicine or dietary supplement. The present invention further provides a method for preparing a mouse with fat-specific overexpression of Metrnl.

4 Claims, 1 Drawing Sheet

METHODS OF REDUCING BLOOD GLUCOSE OR TRIGLYCERIDE LEVELS BY ADMINISTRATION OF METRNL PROTEIN

CROSS REFERENCE TO RELATED APPLICATIONS

This application is a divisional of U.S. application Ser. No. 15/137,606, filed Apr. 25, 2016, which is a continuation of PCT application No. PCT/CN2014/000949, which was filed on Oct. 27, 2014 based on Chinese Patent Application No. 201310525181.5 filed on Oct. 29, 2013 and Chinese Patent Application No 201310525184.9 filed on Oct. 29, 2013, the contents of which are incorporated herein by reference.

TECHNICAL FIELD

The present invention relates to the field of medicine, specifically, application of metrnl protein in preparing hypolipidemic, hypoglycemic medicine.

BACKGROUND ART

METRNL is a novel protein encoded by gene Metrnl, with a molecular weight about 30 kDa. The amino acid sequence of human METRNL was displayed in protein database of National Center for Biotechnology Information with sequence number NP_001004431.1. The tissue expression pattern and functions of Metrnl were seldom researched.

China Application of application No. CN200980137344.4 named "Therapeutic use of a growth factor METRNL" with Published Number CN102164611A showed that METRNL was also a kind of neural survival and growth factor with a role in neuronal protection and/or neural development. Hence, METRNL protein can be used for the treatment of diseases, disorders, or damages of the nervous system.

Diabetes is a metabolic disease characterized by high blood glucose due to insulin deficiency, insulin resistance or both of them. The high blood glucose in diabetes results in chronic damage and dysfunction to various tissues, especially eye, kidney, heart, blood vessel and nerve. Thus, developing new hypoglycemic drug is a hotspot and keystone in drug development.

Bodies of evidence demonstrate that hyperlipemia is an important risk factor for metabolic and cardiovascular diseases, such as type 2 diabetes, glucose intolerance, hypertension and atherosclerosis. Hence, it is meaningful to find new hypolipidemic target or drug.

So far, there have been no reports about the roles of Metrnl protein in preparation of hypoglycemic or hypolipidemic drugs.

SUMMARY OF THE INVENTION

The purpose of this invention is to provide a new use of Metrnl protein.

The present invention provides an application of Metrnl protein in preparing hypoglycemic medicine or dietary supplement.

The present invention provides an application of Metrnl protein in preparing hypolipidemic medicine or dietary supplement.

The present invention further provides a method for preparing Metrnl adipose-specific overexpression mice, comprising the following steps:

constructing plasmid Fabp4-Metrnl containing the promoter region of Fabp4 and open reading frame of Metrnl, injecting the plasmid into fertilized eggs after the verification with sequencing and linearization with restriction enzyme cutting, transplanting the fertilized eggs into the uterus of pseudopregnant mice, choosing the mice carrying the Fabp4-Metrnl in genome to mate with C57BL/6 mice after genomic identification of the offspring, selecting the next-generation mice carrying the Fabp4-Metrnl in genome which is the Metrnl adipose-specific overexpression mice.

The intraperitoneal injection glucose tolerance test in the present invention showed that the blood glucose rose quickly after intraperitoneal injection of glucose in both wild type and Metrnl adipose-specific overexpression mice. And we found that the blood glucose was dramatically lower in Metrnl adipose-specific overexpression mice than that in control wild type mice, indicating that adipose-specific overexpression of Metrnl inhibits the rise of blood glucose, and the Metrnl protein has the hypoglycemic function.

Both control wild type mice and Metrnl adipose-specific overexpression mice were administrated with triglyceride by gavage. The results showed that the blood triglyceride was significantly lower in Metrnl adipose-specific overexpression mice than that in wild type mice. This indicates that the Metrnl protein has the hypolipidemic function.

The Metrnl protein of the present invention can be prepared into a pharmaceutical composition by admixing the Metrnl protein as active ingredient with pharmaceutically acceptable adjuvants.

The pharmaceutically acceptable adjuvants refer to the customary pharmaceutical adjuvants in the pharmaceutical field. Among them, the excipients and diluents include water, etc. The adhesives include cellulose derivatives, gelatin, polyvinylpyrrolidone, etc. The fillers include starch, etc. The crack agents include calcium carbonate and sodium bicarbonate. The compositions can also include adjuvants such as sweetening or flavoring agents.

The pharmaceutical composition including the Metrnl protein as active ingredient and pharmaceutically acceptable adjuvants may be formulated by conventional means known to people skilled in the medical field into a suitable dosage form.

The pharmaceutical composition for oral administration can be prepared into conventional solid formulations such as tablets, powders and capsules, etc.

The pharmaceutical composition for injection can be prepared into injections, etc. The total active ingredients in such formulations comprise from 0.1 to 99.9 percent by weight, preferably from 0.5 to 90 percent by weight.

The said pharmaceutical composition can be used to reduce blood glucose and blood lipid levels of hyperlipemia individuals and the individuals with other disease reasons.

According to the dosage form, the compositions can be administered to the individual in need of a treatment by intraperitoneal injection, subcutaneous injection, intravenous injection, intramuscular injection, lymph node injection, mucosal administration, etc. The individual in need of a treatment according to the invention could be any individual, such as human and animal. The dosage may vary according to the administration routes, ages and conditions of a patient, etc. And it is usually in the range of about 0.01 to 1000 mg/kg/day.

In the description of this invention, Metrnl is a protein with a molecular weight about 30 kDa. The amino acid sequence of human Metrnl was displayed in protein database of National Center for Biotechnology Information with sequence number NP 001004431.1. The present invention has the following effects:

The present invention provides an application of Metrnl protein in preparing hypoglycemic medicine. Metrnl protein can prevent the increase of blood glucose induced by intraperitoneal injection of glucose. This may have a great significance in the treatment of diabetes.

The present invention provides an application of Metrnl protein in preparing hypolipidemic medicine. Metrnl protein can prevent the increase of blood lipid induced by oral high lipid food. This may have a great significance in the treatment of hyperlipidemia.

According to the present information that have been collected, Metrnl protein is an endogenous protein with little side effect to human, thus Metrnl protein is a potential safe pharmaceutical.

DETAILED DESCRIPTION OF THE PREFERRED EMBODIMENTS

The details of this invention are described as following through combination of the embodiments and figures.

The normal mice were purchased from Shanghai Research Center for Model Organisms.

All the reagents and raw materials can be obtained through purchase from companies or preparation with the methods reported. In the following experiments, the processes without specific instructions were carried out routinely or according to the manufactory's instruction.

Embodiment 1: Preparation of Metrnl Adipose-Specific Overexpression Mice

A plasmid containing Fabp4-Metrnl was constructed with the promoter region of Fabp4 and open reading frame of Metrnl. After the verification with sequencing and linearization with restriction enzyme cutting, this plasmid was injected into fertilized eggs which were transplanted into the uterus of pseudopregnant mice. After genomic identification of the offspring, the mice carrying the Fabp4-Metrnl in genome were chosen to mate with C57BL/6 mice. The next-generation mice carrying the Fabp4-Metrnl in genome were selected into experimental group, and the mice without Fabp4-Metrnl in genome were selected into control group.

Plasmid containing Fabp4-Metrnl can also be produced using purchased commodities, for example, open reading frame of Metrnl can be purchased from Thermo (Lot. MMM1013-202763251), and the promoter region of Fabp4 can be obtained from Addgene (No. 11424).

The Metrnl adipose-specific overexpression mice can also produced through entrusting Shanghai Research Center for Model Organisms.

Embodiment 2: Metrnl Overexpression can Prevent the Uncrease of Blood Glucose Induced by Intraperitoneal Injection of Glucose Mice aged 22 weeks have been fed for 16 weeks with high fat diet (Research Diets, Lot. D12492). Both control wild type and Metrnl adipose-specific overexpression mice were administrated with the same dose of glucose via intraperitoneal injection. Follows are the details.

Mice aged 22 weeks fasted for 8 hours, and were intraperitoneally injected with glucose at a dose of 1 g/kg. Then, blood glucose was detected at different time points (Table 1) with a one touch ultra glucometer (Johnson & Johnson) via tail vein bleeding.

Figure 1:
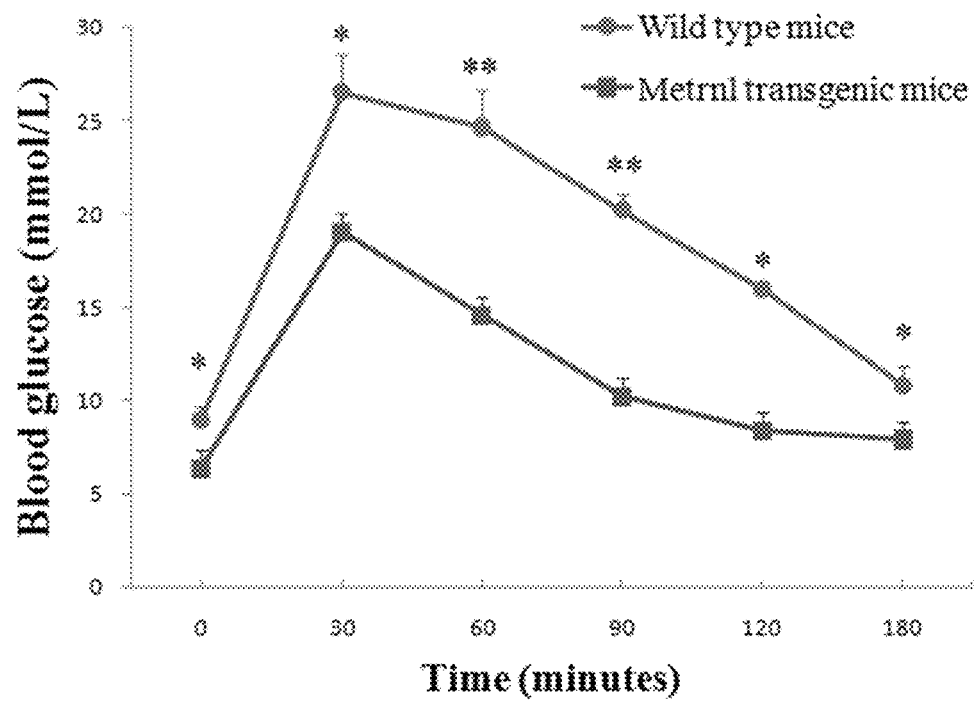
FIG. 1. Blood glucose levels in control wild type mice and Metrnl adipose-specific overexpression transgenic mice after intraperitoneal injection of glucose.

The results showed that the blood glucose was dramatically lower in Metrnl adipose-specific overexpression mice than that in control wild type mice (Table 1 and FIG. 1).

TABLE 1

Adipose-specific overexpression of Metrnl reduces the basal level of blood glucose and inhibits the rise of blood glucose induced by intraperitoneal injection of glucose

| Time after intra- peritoneal injection of glucose (minutes) | Blood glucose (mmol/L) | | Reduction of blood glucose in Metrnl overexpression mice comparing with wild type mice (%) |
|---|---|---|---|
| | Wild type mice + intraperitoneal injection of glucose (n = 8) | Metrnl overexpression mice + intraperitoneal injection of glucose (n = 8) | |
| 0 | 9 ± 0.6 | 6.32 ± 0.8* | 29.8 |
| 30 | 26.44 ± 2.1 | 18.98 ± 0.9* | 28.2 |
| 60 | 24.6 ± 1.9 | 14.52 ± 0.8** | 41.0 |
| 90 | 20.18 ± 0.8 | 10.18 ± 0.8** | 49.6 |
| 120 | 15.98 ± 0.3 | 8.36 ± 0.4* | 47.7 |
| 180 | 10.78 ± 1.0 | 7.88 ± 0.7* | 26.9 |

*Significantly statistical difference existed between Metrnl overexpression mice and control wild type mice ($P < 0.05$).
**Very significantly statistical difference existed between Metrnl overexpression mice and control wild type mice ($P < 0.01$).

Embodiment 3: Metrnl Overexpression can Prevent Hyperlipemia Induced by Gavage with Lipid Both control wild type mice and Metrnl adipose-specific overexpression mice aged 12 weeks were administrated with triglyceride by gavage. Follows are the details.

12-week-old mice fasted for 3 hours, and were administrated with fat emulsion (Lipofundin, B. Braun Melsungen) at a dose of 10 μg. Blood samples were obtained from the tail vein at different time points. And 10 μl serum was used to detect the concentration of triglyceride with Triglyceride Colorimetric Assay Kit (E1003, Applygen Technologies Inc.)

Figure 2:
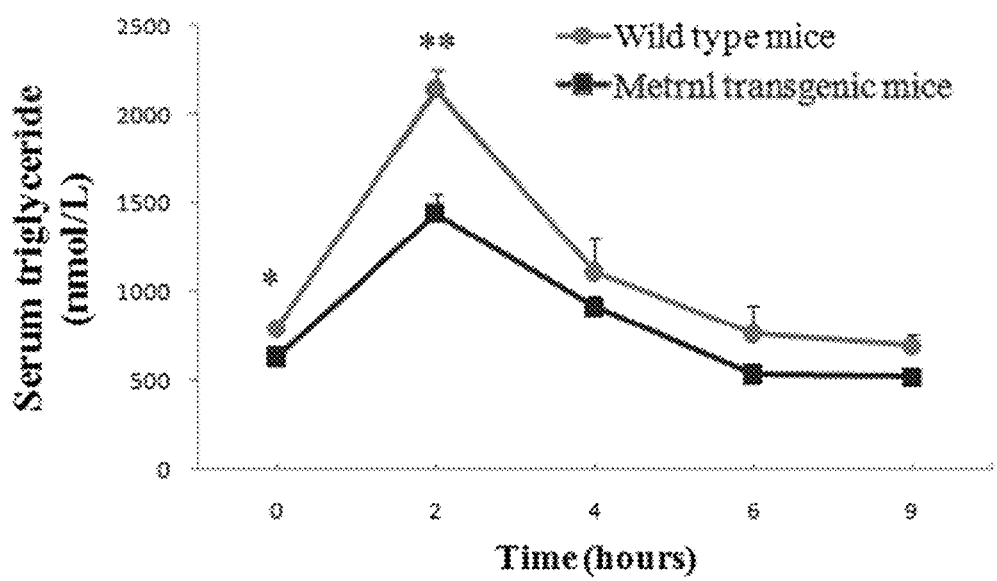
FIG. 2. Blood triglyceride levels in control wild type mice and Metrnl adipose-specific overexpression transgenic mice after triglyceride gavage.

The results showed that the blood triglyceride was significantly lower in Metrnl adipose-specific overexpression mice than that in control wild type mice (Table 2 and FIG. 2).

TABLE 2

Adipose-specific overexpression of Metrnl reduces the basal level of blood triglyceride and prevents the increase of blood triglyceride induced by gavage with fat emulsion

| Time after gavage with fat emulsion (hours) | Serum triglyceride (nmol/L) | | Reduction of blood triglyceride in Metrnl overexpression mice comparing with wild type mice (%) |
|---|---|---|---|
| | Wild type mice + gavage with fat emulsion (n = 8) | Metrnl overexpression mice + gavage with fat emulsion (n = 8) | |
| 0 | 792.0 ± 23 | 636.4 ± 41* | 19.6 |
| 2 | 2137.1 ± 113 | 1437.5 ± 110** | 32.7 |

TABLE 2-continued

Adipose-specific overexpression of Metrnl reduces the basal level of blood triglyceride and prevents the increase of blood triglyceride induced by gavage with fat emulsion

| Time after gavage with fat emulsion (hours) | Serum triglyceride (nmol/L) | | Reduction of blood triglyceride in Metrnl overexpression mice comparing with wild type mice (%) |
|---|---|---|---|
| | Wild type mice + gavage with fat emulsion (n = 8) | Metrnl overexpression mice + gavage with fat emulsion (n = 8) | |
| 4 | 1112.6 ± 184 | 914.7 ± 66 | 17.8 |
| 6 | 767.4 ± 155 | 539.9 ± 13 | 29.6 |
| 9 | 697.0 ± 65 | 526.9 ± 51 | 24.4 |

*Significantly statistical difference existed between Metrnl overexpression mice and control wild type mice ($P < 0.05$).
**Very significantly statistical difference existed between Metrnl overexpression mice and control wild type mice ($P < 0.01$).

The present invention is not intended to limit to embodiments thereof. Further, it will be understood by those skilled in the art that various changes in form and details may be made therein without departing from the spirit and scope of the invention as defined by the appended claims.

The invention claimed is:

1. A method for reducing blood glucose levels of an individual in need thereof comprising administering to the individual a Metrnl protein.

2. A method for reducing blood triglyceride levels of an individual in need thereof comprising administering to the individual a Metrnl protein.

3. A method for treating an individual with diabetes comprising administering to the individual a Metrnl protein.

4. A method for treating an individual with hyperlipidemia comprising administering to the individual a Metrnl protein.

* * * * *